United States Patent [19]

Fazio et al.

[11] Patent Number: 4,500,728

[45] Date of Patent: Feb. 19, 1985

[54] PROCESS FOR PREPARING 2-AMINOETHYL METHACRYLATE SALTS OF HIGH PURITY

[75] Inventors: Michael J. Fazio, Midland, Mich.; Kirk E. Paisley, Newark, Ohio

[73] Assignee: The Dow Chemical Company, Midland, Mich.

[21] Appl. No.: 138,622

[22] Filed: Apr. 8, 1980

[51] Int. Cl.$^3$ ............................................. C07C 69/54
[52] U.S. Cl. .................................................... 560/222
[58] Field of Search .......................................... 560/222

[56] References Cited

U.S. PATENT DOCUMENTS 3,466,308 9/1969 Wehrmeister et al. ............. 542/455
3,505,297 4/1970 Sheetz et al. .

OTHER PUBLICATIONS

Adams, Roger et al., "Organic Reactions", vol. 5, pp. 79, 82 and 86.
Adams, Roger et al., "Organic Reactions", vol. 10 at page 182, (Wiley, Publ.).
Frump, John A., *Chemical Reviews,* vol. 71, pp. 483–505, (1971).
Fieser and Fieser, "Organic Chemistry", (1944), D. C. Heath & Co., Publ., pp. 182 and 242.

*Primary Examiner*—Natalie Trousof
*Assistant Examiner*—L. Hendriksen
*Attorney, Agent, or Firm*—Michael L. Glenn; Charles J. Enright

[57] ABSTRACT

The title salts are prepared in high purity by contacting in an aqueous reaction medium (a) 2-isopropenyl-2-oxazoline present in its free form in low concentration and (b) an acid selected from the group consisting of hydrochloric acid, hydrobromic acid, phosphoric acid, sulfuric acid, nitric acid, organic carboxylic acids, alkyl or aryl sulfonic acids and mixtures thereof. The low concentration of 2-isopropenyl-2-oxazoline (IPO) in its free form can be achieved by adding the IPO slowly to the reaction mixture so that it does not accumulate or by maintaining a pH of less than about 2.5 in the reaction mixture so that nearly all of the IPO will be protonated.

8 Claims, No Drawings

PROCESS FOR PREPARING 2-AMINOETHYL METHACRYLATE SALTS OF HIGH PURITY

BACKGROUND OF THE INVENTION

This invention relates to a process for preparing 2-aminoethyl methacrylate salts of high purity by the reaction of 2-isopropenyl-2-oxazoline with an acid.

Previously, these compounds have been prepared by reacting ethanolamine with a lower alkyl ester of methacrylic acid or with methacryloyl chloride; by reacting ethylenimine (aziridine) with methacrylic acid, as per U.S. Pat. No. 3,336,358; or by acid hydrolysis of an acryloxyalkylketimine, as per U.S. Pat. No. 3,037,969. Such prior art processes were plagued by low yield and/or a production of an impure and highly colored reaction product.

Sheetz and Steiner (U.S. Pat. No. 3,505,297—column 5, lines 45–57) teach that 2-alkenyl-2-oxazolines can be hydrolyzed under "moderate conditions" with either acid or base hydrolysis. Acid hydrolysis is said to result in the formation of 2-aminoethyl acrylates or methacrylates from the 2-vinyl- or 2-isopropenyl-2-oxazoline, respectively. No further reaction conditions were given but they must have been something less rigorous than the acid hydrolysis condition set forth by Wehrmeister in U.S. Pat. No. 3,466,308. Wehrmeister teaches that the 2-alkenyl-2-oxazolines are hydrolyzed to alkenoic acids by refluxing the oxazoline reactants in water in the presence of an acid catalyst. The acid hydrolysis of other oxazolines is taught by Frump in *Chemical Reviews*, 71, 483–505 (1971) at page 494.

SUMMARY OF THE INVENTION

It has now been discovered that 2-aminoethyl methacrylate salts of high purity can be prepared by reacting by contacting in a liquid aqueous medium (a) 2-isopropenyl-2-oxazoline and (b) an acid selected from the group consisting of hydrochloric acid, hydrobromic acid, phosphoric acid, sulfuric acid, nitric acid, organic carboxylic acids, alkyl or aryl sulfonic acids and mixtures thereof, said 2-isopropenyl-2-oxazoline being present essentially continuously in its free form in very low concentration.

The term "very low concentration of free 2-isopropenyl-2-oxazoline", as it is employed herein, refers to a concentration of this oxazoline in its free form no greater than that present in an aqueous medium at a pH of about 2.5, preferably no greater than that present at a pH of about 1.5. Based on the pKa of the 2-isopropenyl-2-oxazoline (5.4), the concentration of this oxazoline at a pH of 2.5 and of 1.5 is calculated to be 0.12 weight percent and 0.012 weight percent, respectively. The term "essentially continuously" refers to the fact that higher concentrations of 2-isopropenyl-2-oxazoline can suitably be present very briefly. For example, when 2-isopropenyl-2-oxazoline is first introduced to an aqueous medium having a pH less than 2.5, a high concentration of the oxazoline in its free form can be present for the brief period prior to protonation of nearly all the 2-isopropenyl-2-oxazoline.

The low concentration of 2-isopropenyl-2-oxazoline in the reaction medium is critical to avoid the formation of by-products during acid hydrolysis of the 2-isopropenyl-2-oxazoline. These recently discovered by-products are believed to be dimers and other oligomers of 2-aminoethyl methacrylate, which are formed by the Michael's Addition of 2-isopropenyl-2-oxazoline to a 2-isopropenyl-2-oxazolinium cation. This dimer can be represented by the formula

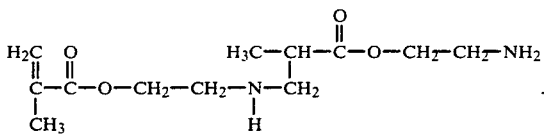

This oligomer impurity deleteriously effects the utility of the 2-aminoethyl methacrylate in such uses as chemical intermediate, flocculant and replacement for ethylenimine in the aminoethylation of polymers.

DETAILED DESCRIPTION OF THE INVENTION

The 2-isopropenyl-2-oxazoline reactant is a known compound and its preparation is well-documented. See, for example, U.S. Pat. No. 3,505,297 or page 490 of the article by Frump cited hereinbefore.

The acid reactants used herein are likewise a known group of compounds. The preferred organic carboxylic acids are the alkanoic acids having from 1 to about 7 carbon atoms or benzoic acid. The preferred sulfonic acids are those bearing an aliphatic or aryl radical having from 1 to about 7 carbon atoms or a benzyl or tolyl radical. Representative organic carboxylic are formic, acetic, propionic, benzoic, polyacrylic and methacrylic acids. Representative sulfonic acids include methanesulfonic and benzenesulfonic acids. Especially preferred as acid reactants are hydrochloric, sulfuric and phosphoric acids.

The instant process is conducted by bringing the acid and 2-isopropenyl-2-oxazoline (IPO) reactants together in a liquid aqueous medium in a manner such that the IPO is present in its free form in very low concentrations during the reaction. The solvent for the aqueous medium can be water alone or it can include a water-soluble cosolvent which is inert in the instant reaction. For example, methanol, ethanol, ethylene glycol or ethylene glycol ethyl ether are suitable as cosolvents. A very low concentration of IPO in the reaction medium can be achieved in one of two ways: (1) by pH control or (2) by slow introduction of the IPO to the medium.

When the acid reactant is a relatively strong acid, the IPO reactant can be added to an aqueous medium containing sufficient acid reactant so that the pH of the medium is preferably in the range from about 0.5 to about 2.5, more preferably about 1.0 to about 1.5. In the foregoing preferred pH ranges, substantially all of the IPO reactant is protonated almost immediately, so that the IPO in its free form is present essentially continuously in very low concentration. Lower pH values than those recited in the foregoing preferred ranges are operable, but not preferred, because these conditions promote the hydrolysis of the resulting 2-aminoethyl methacrylate salt to methacrylic acid and monoethanolamine.

The second procedure which maintains a very low concentration of IPO in the free form is to introduce IPO to an aqueous acid reactant at a rate which does not exceed the rate of hydrolysis of the IPO. The concentration of free IPO can thereby be maintained at very low levels throughout the reaction or during that portion of the reaction in which the pH of the medium is higher than about 2.5. This procedure is especially preferred with weak acids, such as phosphoric acid. The rate of hydrolysis of the IPO increases with temperature. Therefore, the IPO can then be introduced at a more rapid rate as the reaction temperature increases without exceeding the maximum permissible concentration of IPO. For example, at a pH of 1.5 the time required for hydrolysis at 5°, 25° and 55° C. is 2450, 310 and 23 minutes, respectively.

By either of the aforementioned procedures, the instantaneous ratio of IPO to the acid reactant present in the aqueous medium can vary during the reaction. However, no more than one equivalent of IPO for each equivalent of acid reactant should be added to the aqueous medium to avoid formation of oligomers. Of course, a large excess of water is generally employed and is advantageous. A considerable excess of the acid reactant can operably be employed to maintain a low pH as desired. The pH of the final product solution is advantageously adjusted to the natural pH of the 2-aminoethyl methacrylate salt at that concentration after the hydrolysis is complete to improve product stability.

The temperature of the aqueous medium during hydrolysis is advantageously in the range from about −5° to about 60° C., preferably about 0° to about 40° C. However, it is desirable that the pH of the medium be at least 1.5 at temperatures above about 25° C., so as to avoid hydrolysis of the 2-aminoethyl methacrylate salt product.

The aqueous reaction medium advantageously contains an effective amount of a conventional vinyl-addition polymerization inhibitor, so as to prevent polymerization of the IPO or the 2-aminoethyl methacrylate salt product. Any one of several conventional inhibitors can be used, but copper chloride is preferred. Other suitable inhibitors include, for example, di-beta-naphthol, hydroquinone, p-hydroxydiphenylamine, N,N'-diphenyl-pheylenediamine, 2,5-di-t-butylhydroquinone, trinitrotoluene, and the like. The amount of inhibitor used will vary depending upon the commound but will normally be included in amounts of from about 0.01 to about 0.2 weight percent, based on the weight of the 2-aminoethyl methacrylate salt.

The 2-aminoethyl merthacrylate salt is conveniently recovered from the reaction mixture by distillation of the volatile reaction mixture components at reduced pressure, by freeze-drying or by other conventional techniques. The 2-aminoethyl methacrylate frequently can be employed in the aqueous medium in which it is prepared.

The following examples are presented to further illustrate the invention. All parts and percentages are by weight unless otherwise indicated.

EXAMPLE 1

An aqueous solution containing 37 percent IPO was added dropwise with stirring to a reaction vessel containing 50 grams of an aqueous 16 percent HCl solution and 5 milligrams of $CuCl_2 \cdot H_2O$ at a temperature of from 0° to 5° C. The addition of IPO was temporarily stopped when the pH of this reaction mixture as determined by conventional techniques reached 1.0. A 10 milliliter sample of the reaction mixture was removed and the addition of IPO resumed. An additional sample of the reaction mixture was removed at pH values for the mixture of 1.5, 2.0 and 3.0. These four samples were then heated at 30° C. for 24 hours to promote hydrolysis.

Each of the samples was analyzed by conventional liquid chromatographic techniques. The yield of 2-aminoethyl methacrylate hydrochloride was 96, 96, 89 and 52 mole percent based on the IPO added at the pH values of 1, 1.5, 2 and 3, respectively.

This example demonstrates that if the rate of addition of IPO is not carefully controlled, it is critical that a pH of substantially less than 3 be maintained to promote the formation of the 2-aminoethyl methacrylate salt in high purity.

On the other hand, it was found that 2.0, 0.4, 0.1 and 0.06 mole percent of methacrylic acid based on the IPO introduced was produced at the pH values of 1, 1.5, 2 and 3, respectively. Therefore, there is a lower limit on the operable pH as well.

EXAMPLE 2

To a 100 milliliter (ml) reaction vessel was charged 18.95 grams of aqueous 38 percent HCl and 4 milligrams of $CuCl_2 \cdot 2H_2O$. An aqueous solution containing 52 percent IPO was added dropwise (1 ml/minute) to the reaction vessel at 0° C. The addition of IPO was terminated when the pH of the reaction mixture reached 1.3, at which time 39.7 grams of the IPO solution had been introduced. The mixture was warmed to 20° C. and maintained at this temperature for 120 hours.

The aqueous reaction mixture was analyzed by conventional liquid chromatographic analysis techniques and was found to contain 0.6 percent methacrylic acid, 0.3 percent N-(2-hydroxyethyl)methacrylamide, 0.15 percent IPO, 48.5 percent 2-aminoethyl methacrylate hydrochloride and 1.3 percent dimer of the 2-aminoethyl methacrylate. Yield of the desired 2-aminoethyl methacrylate salt was 92.5 mole percent based on IPO.

EXAMPLE 3

In the same manner as in Example 2, 33.3 grams of aqueous 49 percent HBr, 43.4 grams of water and 4 milligrams of $CuCl_2 \cdot H_2O$ were charged to a 250 ml reaction vessel. An aqueous 52 percent IPO was added dropwise to the reaction vessel at 0° C. to effect a pH of 1.25, at which time 40.8 grams of the IPO solution had been introduced. The mixture was warmed to 20° C. and maintained at that temperature for 100 hours.

The aqueous reaction mixture was analyzed by conventional liquid chromatographic analysis techniques and was found to contain 0.13 percent methacrylic acid, 0.14 percent N-(2-hydroxyethyl)methacrylamide, 0.22 percent IPO, 32.3 percent 2-aminoethyl methacrylate hydrobromide salt and 0.35 percent dimer of the 2-aminoethyl methacrylate. The yield of the desired product is 95 mole percent based on IPO.

EXAMPLE 4

To a 1-liter reaction vessel was charged 115.5 grams of aqueous 85 percent phosphoric acid, 320.9 grams of water and 24 milligrams of $CuCl_2 \cdot H_2O$. An aqueous solution containing 83 percent IPO was added dropwise to the mixture in the reaction vessel until a pH of 1.2 was attained, at which time 48 grams of 83 percent IPO had been added. The reaction mixture was heated to 50°–55° C. and the addition of IPO resumed at an average rate of about 0.1 ml per minute. The addition of IPO was terminated when the pH of the reaction mixture was 3.5, at which time a total of 132 grams of IPO was added in the two additions.

The aqueous reaction mixture was analyzed by conventional liquid chromatographic analysis techniques and was found to contain 0.34 percent methacrylic acid, 0.06 percent N-(2-hydroxyethyl)methacrylamide, 31.7 percent 2-aminoethyl methacrylate salt and 5.7 percent dimer of the 2-aminoethyl methacrylate. The yield of the desired salt is 80 mole percent based on IPO.

EXAMPLE 5

To a reaction vessel was charged 9.8 grams of aqueous 38 percent HCl, 25 grams of ethylene glycol ethyl ether and 4 milligrams of $CuCl_2 \cdot H_2O$. An aqueous 57 percent solution is added to the reaction vessel at a temperature of 0°–5° C. to effect a pH of 1.25, at which time 18.8 grams of IPO had been introduced. The reaction mixture was warmed to 30° C. and maintained at that temperature for 15 hours.

The reaction mixture was analyzed by conventional liquid chromatographic analysis techniques and was found to contain 27 percent 2-aminoethyl methacrylate hydrochloride salt. The yield of the desired product was 95 mole percent based on IPO.

What is claimed is:

1. A process for preparing 2-aminoethyl methacrylate of high purity comprising introducing 2-isopropenyl-2-oxazoline to a liquid aqueous medium containing an acid selected from the group consisting of hydrobromic acid, phosphoric acid, sulfuric acid, nitric acid, organic carboxylic acids, sulfonic acids and mixtures thereof; at a rate to maintain a continuous concentration of no greater than about 0.12 weight percent 2-isopropenyl-2-oxazoline in its free form in the medium.

2. The process as described in claim 1 wherein the acid reactant is an alkanoic acid having from 1 to about 7 carbon atoms or benzoic acid.

3. The process as described in claim 1 wherein the acid reactant is a sulfonic acid bearing an aliphatic or aryl radical having from 1 to about 7 carbon atoms or a tolyl or benzyl radical.

4. The process as described in claim 1 wherein the acid reactant is sulfuric or phosphoric acid.

5. The process as described in claim 1 wherein the pH of the liquid aqueous medium is in the range from about 0.5 to about 1.5 during the reaction.

6. The process as described in claim 5 wherein the temperature of the aqueous medium is in the range from about −5° C. to about 60° C.

7. The process as described in claim 1 wherein a water-soluble cosolvent selected from the group consisting of methanol, ethanol, ethylene glycol and ethylene glycol ethyl ether is present in the aqueous medium.

8. The process as described in claim 1 wherein the aqueous reaction medium contains an effective amount of a vinyl polymerization inhibitor.

* * * * *